United States Patent [19]

Radtke et al.

[11] Patent Number: 5,204,256
[45] Date of Patent: Apr. 20, 1993

[54] PROCESS FOR THE PURIFICATION OF PLASMINOGEN ACTIVATOR INHIBITOR 2 (PAI-2)

[75] Inventors: Klaus-Peter Radtke, La Jolla, Calif.; Norbert Heimburger, Marburg; Karlheinz Wenz, Weimar, both of Fed. Rep. of Germany

[73] Assignee: Behringwerke Aktiengesellschaft, Marburg, Fed. Rep. of Germany

[21] Appl. No.: 892,634

[22] Filed: Jun. 2, 1992

Related U.S. Application Data

[63] Continuation of Ser. No. 719,078, Jun. 19, 1991, abandoned, which is a continuation of Ser. No. 577,632, Sep. 4, 1990, abandoned.

[30] Foreign Application Priority Data

Sep. 6, 1989 [DE] Fed. Rep. of Germany ....... 3929504

[51] Int. Cl.$^5$ ........................... C12N 9/50; C12N 9/64
[52] U.S. Cl. .................................... 435/226; 435/219; 435/814
[58] Field of Search .................. 435/226, 219, 814

[56] References Cited

U.S. PATENT DOCUMENTS

| | | | |
|---|---|---|---|
| 4,530,787 | 7/1985 | Shaked et al. | 424/85.2 |
| 4,563,417 | 1/1986 | Albarella et al. | 435/6 |
| 4,572,798 | 2/1986 | Koths et al. | 424/85.6 |
| 4,677,196 | 6/1987 | Rausch et al. | 435/69.4 |
| 4,892,826 | 1/1990 | Homandberg et al. | 435/183 |
| 4,923,807 | 5/1990 | Webb et al. | 435/69.2 |

FOREIGN PATENT DOCUMENTS

PCT/AU85/-
00191  2/1986  PCT Int'l Appl. ............... 435/69.2

OTHER PUBLICATIONS

T. Stief et al., "Evidence for Identity of PCI and Plasminogen Activator Inhibitor 3", Biol. Chem. Hoppe-Seyler 368: 1427–1433 (1987).

*Primary Examiner*—David M. Naff
*Assistant Examiner*—Michael V. Meller
*Attorney, Agent, or Firm*—Finnegan, Henderson, Farabow, Garrett & Dunner

[57] ABSTRACT

A process for the purification of plasminogen activator inhibitor 2 (PAI-2) including the steps of preincubating a PAI-2-containing solution with a compound which cleaves disulfide linkages, mixing the solution with a water-soluble acridine or quinoline base to precipitate impurities in the solution, and separating the precipitated impurities to obtain PAI-2 in purified form.

12 Claims, No Drawings

PROCESS FOR THE PURIFICATION OF PLASMINOGEN ACTIVATOR INHIBITOR 2 (PAI-2)

This application is a continuation of application Ser. No. 07/719,078, filed Jun. 19, 1991, now abandoned, which is a continuation of application Ser. No. 07/577,631, filed on Sep. 4, 1990, now abandoned.

The invention relates to a process for the purification of plasminogen activator inhibitor 2 (PAI-2), wherein impurities are precipitated with an acridine or quinoline base.

Plasminogen activators (PA) are serine proteases which activate the fibrinolytic system. They convert the inactive proenzyme plasminogen into the active enzyme plasmin which degrades fibrin and fibrinogen. In the body there are two PA, the tissue plasminogen activator (t-PA) and the PA which is identical with urokinase (u-PA) and which is produced by renal cells but also other normal or malignant cells. The t-PA possesses particular importance in the prevention of thromboses. u-PA prevents formation of fibrin clots in the urinary tract but also contributes to the healing of wounds and has been found where there is neoplastic growth.

The concentration and activity of the PA are regulated by their synthesis but also by inhibitors. Two specific PA inhibitors (PAI) which do not inhibit plasmin or other proteases are known. One of them is produced in endothelial cells (PAI-1), the other one found in placenta (PAI-2) has also been called "minactivin".

Starting from an extract from placenta a 120-fold concentration of PAI-2 can be achieved according to the state of the art by an ammonium sulfate fractionation, adsorption of impurities on CM-Sephadex C-50, a gel filtration and hydroxya-patite chromatography. This process results in two forms of PAI-2 with molecular weights of 70 and 43 kDa. Immunoaffinity chromatography and a combination of immunoaffinity chromatography and FPLC have also been used for purification. A combination of 8 process steps comprising a precipitation with neutral salts, chromatographies on CM- and DEAE- ®Sepharose and hydroxyapatite, and a preparative electrophoresis led, starting from placenta, to a pure PAI-2 with a molecular weight of 47 kDa. It has also been known that chromatographic purification steps can be influenced advantageously by the addition of reducing agents of the dithiothreitol type.

The object of the invention is to find a simpler process which can be used on the production scale for the isolation of PAI-2.

Surprisingly it has been that impurities can be precipitated from a solution of PAI-2 using 2-ethoxy-6,9-diaminoacridine lactate while the PAI-2 itself remains in solution in the supernatant.

A preincubation with dithiothreitol (DTT) proved to be advantageous.

The invention relates to a process for the purification of plasminogen activator inhibitor 2 (PAI-2), which comprises a PAI-2-containing solution being preincubated with an agent cleaving disulfide linkages, preferably dithiothreitol (DTT), and being mixed with a suitable, water-soluble acridine or quinoline base, preferably 2-ethoxy-6,9-diaminoacridine lactate, in such an amount that the precipitate formed does not contain more than a little PAI-2, this precipitate being separated off, and the PAI-2 being obtained from the supernatant and, where appropriate, further purified using known processes.

PAI-2 will also precipitate if small amounts of acridine or quinoline base in relation to the amount of proteins in solution are added. An appropriate concentration of a water-soluble salt of the base, preferably 2-ethoxy-6,9-diaminoacridine lactate, is from 200 mg to 2 g/g of protein in solution (PAI-2 remains substantially in solution). The process is carried out at a pH of 5.5–8.5.

The PAI-2-containing solution may have been pasteurized beforehand, where appropriate with the addition of stabilizers, preferably glycine and/or sucrose.

The PAI-2-containing solution is preferably an extract of placenta or a solution containing genetically engineered PAI-2.

The disulfide-cleaving agent is used in a concentration of from 10 mmol/l to 250 mmol/l, preferably 100 mmol/l. Preincubation is carried out for from 15 min to 3 hours, preferably for 1 hour, at 10° to 40° C., preferably about 37° C.

85–90% of the employed PAI-2 activity, but only 5–8% of the employed amount of protein, are present in the supernatant when the process is carried out as described.

After the precipitation the acridine base can be salted out of the supernatant, preferably using NaCl, preferably 5%, and the PAI-2 can be concentrated by an ammonium sulfate precipitation, for example by 80% saturation of the solution with ammonium sulfate, which yields an additional purification in combination with a preliminary precipitation at 30% saturation of the solution with ammonium sulfate. Since about 90% of the employed protein are removed by the Rivanol and ammonium sulfate precipitation, the small residual amount can then be subjected to purification processes which are subject to volume limitation: for example a chromatography on DEAE- ®Affigel Blue, a chromatography gel with bifunctional affinity which is composed of diethylaminoethyl groups and ®Cibacron Blue F3GA dye covalently bonded to agarose, and on hydroxyapatite Material of this degree of purity should already be suitable for therapeutic use. Ultrapurification can be carried out by hydrophobic chromatography on a phenylalanine column but is associated with substantial losses.

The PAI-2 which is obtained may additionally be pasteurized, if this has not been done beforehand.

The process according to the invention is described hereinafter:

An amidolytic method was used in combination with the chromogenic substrate S-2444 (Glu-Gly-Arg-pNA) from Kabi for monitoring the isolation of PAI-2. For the determination, 50 µl of urokinase (u-PA) (1000 U/ml) were incubated with 100 µl of PAI-2-containing sample for 4 min at room temperature, and 80 µl of this mixture were transferred into a plastic cuvette which had been prewarmed to 37° C. 50 µl of buffer A and 20 µl of S-2444 (6 mM) were then added. The increase in absorption at 405 nm was determined in a Cobas Bio centrifugal analyzer. The measurements were evaluated by comparison with a dilution plot which had been constructed via serial dilution of an in-house PAI-2 standard.

Materials which were used for the isolation of PAI-2:
2-Ethoxy-6,9-diaminoacridine lactate (6,9-diamino-2-ethoxyacridine lactate): Sigma Chemie GmbH, D-6100 Darmstadt; a 2.5% (w/v) strength solution in 12.5 mM tris, pH 6.8, was used for the fractional precipitation.

Dithiothreitol (DTT): Serva Feinbiochemika GmbH & Co., D-6900 Heidelberg

Hydroxyapatite: ®BioRad, Richmond, Calif., USA

Phenylalanine- ®Sepharose and CNBr-activated ®Sepharose 4B: Deutsche Pharmacia GmbH, D-6900 Freiburg S-2444: Kabi Vitrum, S-11287 Stockholm, Sweden Tris(hydroxymethyl)aminomethane (tris): E. Merck, D-6100 Darmstadt Urokinase (®Actosolv): Behringwerke AG, D-3550 Marburg Buffer A: 50 mM tris, pH 8.4, 1% polygeline, 100 mM NaCl, 0.01% ®Triton×100 and 0.01% NaN$_3$ Buffer B: 20 mM tris, pH 7.5, 20 mM DTT Buffer C: 20 mM Na$_2$HPO$_4$, pH 6.8, 20 mM DTT Buffer D: 20 mM tris, pH 7.5, 20 mM DTT, 30% saturation with ammonium sulfate Buffer E: 20 mM tris, pH 7.5, 100 mM NaCl Buffer F: 20 mM tris, pH 6.8

EXAMPLE

Frozen human placenta which had been washed free from blood was used as raw material for the preparation of PAI-2; the placenta had been chopped up in a cutter and then extracted with 0.5% NaCl and 3 mM EDTA. The remnants of cells were removed by centrifugation and the supernatant was precipitated with 8% Rivanol, and the precipitate was dissolved and subjected to a fractional precipitation with ammonium sulfate. The precipitate which contained the PAI-2 was dissolved in buffer F and dialyzed against it. The concentrated extract of placenta contained 4,615 U of PAI-2/ml with a specific activity of 120 U/mg. This material was used for the ultrapurification.

Rivanol and Ammonium Sulfate Precipitation 500 ml of the starting material described above (Tab. 1) were incubated with 7.7 g of DTT (final concentration 100 mM) at 37° C. for 1 hour. 1,520 ml of a 2.5% strength Rivanol solution were added dropwise to this solution while continuously stirring cautiously, thus reaching a final concentration corresponding to 200%. The precipitate resulting from the precipitation was removed by centrifugation, and excess Rivanol was removed from the supernatant by addition of 100 g of solid NaCl to final concentration of 5%. 343 g of solid ammonium sulfate were then added to the supernatant until a final concentration corresponding to 30% saturation was reached. The precipitate was removed by centrifugation (20 min, 3000 rpm), and 694 g of solid ammonium sulfate were then added to a final concentration of 80% saturation. The precipitate resulting from this was dissolved buffer B in high concentration and dialyzed. This resulted in 80 ml of dissolved and dialyzed ammonium sulfate residue.

DEAE- ®Affigel Blue Chromotography 80 ml of the ammonium sulfate precipitate were applied to a DEAE-Affigel Blue column (17.5×4.4 cm, 260 ml gel bed) which had been equilibrated with buffer B. The column was eluted using an NaCl gradient in buffer B (2×1000 ml) which covered a range from 0 to 200 mM NaCl at a flow rate of 90 ml/h. The protein concentration was continuously measured via the OD at 280 nm and the PAI-2 activity was determined as described.

Hydroxyapatite Chromatography 472 ml of the PAI-2-containing fractions from the previous step were collected, dialyzed against buffer C and applied to a hydroxyapatite column (15×3.2 cm, 56 ml gel bed) (Table 1) which had been equilibrated with the same buffer. The column was eluted at a flow rate of same buffer. The column was eluted at a flow rate of 50 ml/h and using a salt gradient of sodium phosphate (0.02 to 0.3M; 2×250 ml) in buffer C. The protein concentration and PAI-2 activity of the eluate were determined continuously.

Phenylalanine- ®Sepharose

The PAI-2-containing fractions after hydroxyapatite chromatography were collected, and 13.2 g of solid ammonium sulfate were added to 120 ml of this material to reach 30% saturation. This solution was applied to a phenylalanine- ®Sepharose column which had been equilibrated with buffer D. The resin was eluted at a flow rate of 20 ml/h and using a gradient formed from buffer D and B (2×100 ml). The PAI-2-containing fractions were collected and characterized. The purest material had a specific activity of 60,000 U (=units)/mg and migrated in SDS polyacrylamide gel electrophoresis as one band which had a molecular weight of 43 kDa and could be demonstrated in an immunoblot with a specific monoclonal antibody.

TABLE 1

| Purification of plasminogen activator inhibitor 2 (PAI-2) | | | | | | |
|---|---|---|---|---|---|---|
| | Volume (ml) | Protein conc. (mg) | PAI-2 activity (U) | Spec. activity (U/mg) | Purification factor | Yield (%) |
| Starting material | 500 | 19,000 | 2.20 × 10$^6$ | 115 | 1 | 100 |
| Rivanol supernatant | 1,850 | 1,311 | 1.80 × 10$^6$ | 1,373 | 11.9 | 82 |
| 30–80% ammonium sulfate residue | 80 | 800 | 1.15 × 10$^6$ | 1,460 | 13 | 52 |
| DEAE-$^R$Affigel Blue | 472 | 65 | 5.90 × 10$^5$ | 9,143 | 79.5 | 27 |
| Hydroxyapatite | 120 | 16.3 | 4.60 × 10$^5$ | 28,100 | 244 | 21 |
| Phenylalanine-$^R$Sepharose | 210 | 2.3 | 1.20 × 10$^4$ | 52,300 | 455 | 5.5 |

We claim:

1. A process for the purification of plasminogen activator inhibitor 2 (PAI-2), which comprises the steps:
   (a) preincubating a PAI-2-containing solution with a compound which cleaves disulfide linkages;
   (b) mixing said solution with a water-soluble acridine or quinoline base to precipitate impurities in the solution; and
   (c) separating the precipitated impurities to obtain PAI-1 in purified form.

2. The process as claimed in claim 1, wherein the PAI-2-containing solution is an extract of placenta or a solution of genetically engineered PAI-2.

3. The process as claimed in claim 1, wherein the disulfide-cleaving compound is dithiothreitol.

4. The process as claimed in claim 1, wherein the disulfide-cleaving compound is used in a concentration of from 10 mmol/l to about 250 mmol/l.

5. The process as claimed in claim 1, wherein preincubation is carried out for 15 min to about 3.

6. The process as claimed in claim 1, wherein said preincubation is carried out at about 10° to about 40° C.

7. The process as claimed in claim 1, wherein the base is used in dissolved form at a pH of about 5.5 to about 8.5.

8. The process as claimed in claim 1, wherein said PAI-2-containing solution is pasteurized.

9. The process according to claim 1, wherein said base is 2-ethoxy-6,9-diaminoacridine lactate.

10. The process according to claim 1,
   wherein separating the precipitated impurities is carried out by filtering, and
   isolating the PAI-2 from the filtrate.

11. The process according to claim 4, wherein the disulfide-cleaving compound is employed in a concentration of about 100 mmol/l.

12. The process according to claim 5, wherein said preincubation is carried out at about 37° C.

* * * * *

UNITED STATES PATENT AND TRADEMARK OFFICE
CERTIFICATE OF CORRECTION

PATENT NO. : 5,204,256
DATED : April 20, 1993
INVENTOR(S) : Klaus-Peter Radtke et al It is certified that error appears in the above-indentified patent and that said Letters Patent is hereby corrected as shown below:

Related U.S. Application Data, Title Page [63], line 2, change "577,632," to --577,631--.

Claim 4, column 5, line 3, after "from" insert --about--.

Claim 5, column 5, line 5, after "for" insert --about-- and after "3" reinsert --hours--.

Signed and Sealed this

Seventeenth Day of May, 1994

Attest:

BRUCE LEHMAN

Attesting Officer

Commissioner of Patents and Trademarks